US012077523B2

United States Patent
Kim et al.

(10) Patent No.: US 12,077,523 B2
(45) Date of Patent: Sep. 3, 2024

(54) N-(ISOPROPYL-TRIAZOLYL)PYRIDINYL)-HETEROARYL-CARBOXAMIDE DERIVATIVES AND USE THEREOF

(71) Applicant: HK INNO.N CORPORATION, Seoul (KR)

(72) Inventors: Dongkyu Kim, Suwon-si (KR); Seungin Kim, Suwon-si (KR); Jaeho Yoo, Hwaseong-si (KR); Seunghee Ji, Suwon-si (KR); Joo-hwan Kim, Seongnam-si (KR); Joonseok Byun, Suwon-si (KR); Jinwoo Jung, Seoul (KR); Soo-jin Kim, Suwon-si (KR); Yeji Byeon, Suwon-si (KR); Jiwon Choi, Icheon-si (KR)

(73) Assignee: HK INNO.N CORPORATION, Seoul (KR)

( * ) Notice: Subject to any disclaimer, the term of this patent is extended or adjusted under 35 U.S.C. 154(b) by 700 days.

(21) Appl. No.: 17/276,490

(22) PCT Filed: Oct. 10, 2019

(86) PCT No.: PCT/KR2019/013311
§ 371 (c)(1),
(2) Date: Mar. 16, 2021

(87) PCT Pub. No.: WO2020/080741
PCT Pub. Date: Apr. 23, 2020

(65) Prior Publication Data
US 2022/0033378 A1  Feb. 3, 2022

(30) Foreign Application Priority Data
Oct. 18, 2018 (KR) .................. 10-2018-0124732

(51) Int. Cl.
C07D 401/14 (2006.01)
C07D 409/14 (2006.01)

(52) U.S. Cl.
CPC ......... *C07D 401/14* (2013.01); *C07D 409/14* (2013.01)

(58) Field of Classification Search
CPC ............... C07D 401/14; C07D 409/14; A61K 31/4439; A61K 31/4427
USPC ........................................................ 544/333
See application file for complete search history.

(56) References Cited

FOREIGN PATENT DOCUMENTS

| CN | 107793400 A | 3/2018 |
|---|---|---|
| JP | 2011-506362 A | 3/2011 |
| JP | 2017-506239 A | 3/2017 |
| JP | 2018-503661 A | 2/2018 |
| WO | 2013/112741 A1 | 8/2013 |
| WO | 2018/151830 A1 | 8/2018 |
| WO | 2018/157857 A1 | 9/2018 |
| WO | 2018/183122 A1 | 10/2018 |
| WO | 2018/233553 A1 | 12/2018 |

OTHER PUBLICATIONS

Office Action dated Jun. 15, 2023, issued in corresponding European Patent Application No. 19874258.7.
International Search Report issued in corresponding International Patent Application No. PCT/KR2019/013311 dated Jan. 20, 2020.
Written Opinion issued in corresponding International Patent Application No. PCT/KR2019/013311 dated Jan. 20, 2020.

*Primary Examiner* — Taylor V Oh
(74) *Attorney, Agent, or Firm* — Morgan, Lewis & Bockius LLP

(57) ABSTRACT

The present disclosure relates to novel N-(isopropyl-triazolyl)pyridinyl)-heteroaryl-carboxamide derivatives or pharmaceutically acceptable salts thereof; a preparation method thereof; and use for preventing or treating an ASK-1 mediated disease comprising the same as an active ingredient.

20 Claims, No Drawings

N-(ISOPROPYL-TRIAZOLYL)PYRIDINYL)-HETEROARYL-CARBOXAMIDE DERIVATIVES AND USE THEREOF

TECHNICAL FIELD

The present disclosure relates to novel N-(isopropyl-triazolyl)pyridinyl)-heteroaryl-carboxamide derivatives or pharmaceutically acceptable salts thereof; a preparation method thereof; and use for preventing or treating an ASK-1 mediated disease comprising the same as an active ingredient.

BACKGROUND ART

Mitogen-activated protein kinase (MAPK) signaling cascades involve in directing various extracellular and intracellular queues to cellular stress responses, including cell growth, differentiation, inflammation, and apoptosis. MAPKs exist in different types such as MAP3Ks, MAP2Ks, and MAPKs. MAP3Ks directly respond to environmental signals and phosphorylate MAP2Ks, which in turn phosphorylates specific MAPKs. Subsequently, MAPKs serve to mediate appropriate cellular responses by phosphorylating cellular substrates, including transcription factors that regulate gene expression.

Apoptosis signal-regulating kinase 1 (ASK1), which is also known as a mitogen-activated protein kinase kinase kinase 5 (MAP3K5), is a member of the MAP kinase kinase kinase (MAP3K) family that activates the c-Jun N-terminal protein kinase (JNK) and p38 MAP kinase.

ASK1 is activated by a series of various stimuli including oxidative stress, reactive oxygen species (ROS), LPS, TNF-α, FasL, endoplasmic reticulum (ER) stress, and intracellular calcium influx, and consequently activates the c-Jun N-terminal protein kinase (JNK) and p38 MAP kinase.

Phosphorylation of ASK1 protein can lead to apoptosis or other cellular responses depending on the cell type. ASK1 activation has been reported to be associated with a broad range of diseases including neurodegenerative diseases, cardiovascular diseases, inflammatory diseases, autoimmune diseases, and metabolic disorders. In addition, ASK1 has been implicated to particularly play a vital role in psychosomatic diseases, for example, kidney diseases, diabetic nephropathy, chronic kidney diseases, fibrosis (including lung fibrosis and kidney fibrosis), respiratory diseases (including chronic obstructive pulmonary disease (COPD) and acute lung injury), and acute and chronic liver diseases.

Therefore, development of therapeutic agents that function to inhibit ASK1 signaling complexes is expected to remedy or improve the lives of patients in need of prevention and treatment of such a broad range of diseases.

DISCLOSURE OF INVENTION

Technical Problem

The present inventors have made extensive efforts to develop novel compounds that can inhibit ASK-1 activity, and as a result, they have confirmed that a series of N-(isopropyl-triazolyl)pyridinyl)-heteroaryl-carboxamide derivative can effectively inhibit ASK-1 activity and thus can be useful in the prevention and treatment of an ASK-1 mediated disease, thereby completing the present invention.

Solution to Problem

An object of the present disclosure is to provide N-(isopropyl-triazolyl)pyridinyl)-heteroaryl-carboxamide derivatives or pharmaceutically acceptable salts thereof.

Another object of the present disclosure is to provide a method for preparing the aforementioned N-(isopropyl-triazolyl)pyridinyl)-heteroaryl-carboxamide derivatives.

Still another object of the present disclosure is to provide a pharmaceutical composition for preventing or treating an ASK-1 mediated disease, including the aforementioned N-(isopropyl-triazolyl)pyridinyl)-heteroaryl-carboxamide derivatives or pharmaceutically acceptable salts thereof as an active ingredient.

Still another object of the present disclosure is to provide a method for preventing or treating an ASK-1 mediated disease, including administering the aforementioned pharmaceutical composition to a subject in need thereof.

Advantageous Effects of Invention

The novel N-(isopropyl-triazolyl)pyridinyl)-heteroaryl-carboxamide derivatives or pharmaceutically acceptable salts thereof exhibit an inhibitory effect against ASK-1 activity and thus can be effectively used in the prevention and treatment of an ASK-1 mediated disease.

BEST MODE FOR CARRYING OUT THE INVENTION

In one aspect of the present disclosure to achieve the above objects, there is provides N-(isopropyl-triazolyl)pyridinyl)-heteroaryl-carboxamide derivatives or pharmaceutically acceptable salts thereof.

In another aspect of the present disclosure, there is provided a method for preparing the N-(isopropyl-triazolyl)pyridinyl)-heteroaryl-carboxamide derivatives.

In still another aspect of the present disclosure, there is provided a pharmaceutical composition for preventing or treating an ASK-1 mediated disease, including the N-(isopropyl-triazolyl)pyridinyl)-heteroaryl-carboxamide derivatives or pharmaceutically acceptable salts thereof as an active ingredient.

In still further another aspect of the present disclosure, there is provided a method for preventing or treating an ASK-1 mediated disease, including administering the pharmaceutical composition to a subject in need thereof.

Hereinbelow, the present disclosure will be described in detail.

Listed below are definitions of various concepts used to describe the compounds of the present disclosure.

These definitions apply to the terms used throughout this specification, unless otherwise limited in specific instances, either individually or as part of a larger group.

The term "alkyl" refers to a straight, branched or cyclic hydrocarbon radical, and each carbon atom may be optionally substituted with one or more substituents.

The term "alkoxy" refers to —O-alkyl, and the alkyl is as defined above.

The term "aryl" refers to an aromatic group including phenyl, naphthyl and the like. Aryl may be optionally substituted with one or more substituents.

The term "heteroaryl" refers to a saturated, partially saturated or aromatic group containing 1 to 4 heteroatoms selected from N, O and S, which can be optionally fused with benzo or cycloalkyl.

The term "halo(gen)" refers to a substituent selected from the group consisting of fluoro, chloro, bromo or iodo.

The terms and abbreviations used herein have their original meanings unless defined otherwise.

The N-(isopropyl-triazolyl)pyridinyl)-heteroaryl-carboxamide derivative of the present disclosure may be a compound represented by Chemical Formula 1 below:

[Chemical Formula 1]

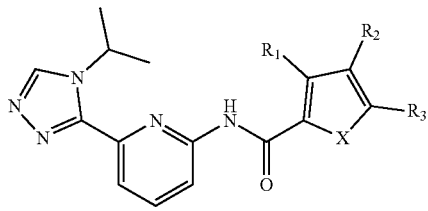

in the Chemical Formula 1,
X is NH, O or S,
R$_1$ is hydrogen, C$_{1-6}$ alkyl, C$_{1-6}$ heteroalkyl, C$_{1-6}$ alkoxy, or halogen, and
R$_2$ and R$_3$ are each independently hydrogen, C$_{1-6}$ alkyl, C$_{1-6}$ heteroalkyl, C$_{1-6}$ alkoxy, halogen, cyano, nitro, amino, C$_{1-6}$ alkoxy-C$_{1-6}$ alkyl, C$_{6-10}$ aryl, C$_{6-10}$ arylamino, C$_{5-10}$ heteroaryl, or C$_{5-10}$ heteroarylamino,
wherein the aryl or heteroaryl is unsubstituted or substituted with at least one selected from the group consisting of C$_{1-6}$ alkyl, C$_{1-6}$ alkoxy, C$_{1-6}$ alkoxy-C$_{1-6}$ alkyl, halogen, nitro, cyano, amino, C$_{1-6}$ alkylamino, acetylamino, formyl, C$_{1-6}$ alkylcarbonyl, morpholinocarbonyl, morpholinyl, piperazinyl, piperidinyl, aminocarbonyl, C$_{1-6}$ alkylaminocarbonyl, di(C$_{1-6}$alkyl)aminocarbonyl, C$_{1-6}$ alkyl-thio, cyano-C$_{1-6}$ alkyl, C$_{1-6}$ haloalkyl, C$_{1-6}$ dihaloalkyl, C$_{1-6}$ alkylsulfonyl, aminosulfonyl, C$_{1-6}$ alkylaminosulfonyl, di(C$_{1-6}$ alkyl)aminosulfonyl, C$_{1-6}$ heteroalkyl, and heteroaryl-C$_{1-6}$ alkyl.

Specifically, in the Chemical Formula 1, X may be NH, and R$_1$ may be hydrogen.

For example, in the Chemical Formula 1, R$_2$ and R$_3$ may be each independently hydrogen, C$_{1-6}$ alkyl, C$_{1-6}$ alkoxy, C$_{1-6}$ alkoxy-C$_{1-6}$ alkyl, C$_{6-10}$ aryl, or C$_{5-10}$ heteroaryl.

Specifically, in the Chemical Formula 1, R$_2$ and R$_3$ may be each independently hydrogen, methyl, ethyl, methoxymethyl, or unsubstituted or substituted phenyl, thiophenyl or pyrimidinyl.

For example, in the compound of the present disclosure, the aryl or heteroaryl may be unsubstituted or substituted with at least one selected from the group consisting of methyl, chloro, fluoro, ethoxy, methylthio and methylsulfonyl, but is not limited thereto.

More specifically, the compound of the present disclosure may be
1. N-(6-(4-isopropyl-4H-1,2,4-triazol-3-yl)pyridin-2-yl)-4-methyl-1H-pyrrole-2-carboxamide,
2. N-(6-(4-isopropyl-4H-1,2,4-triazol-3-yl)pyridin-2-yl)-4-m-tolyl-1H-pyrrole-2-carboxamide,
3. N-(6-(4-isopropyl-4H-1,2,4-triazol-3-yl)pyridin-2-yl)-4-(methoxymethyl)-1H-pyrrole-2-carboxamide,
4. 4-ethyl-N-(6-(4-isopropyl-4H-1,2,4-triazol-3-yl)pyridin-2-yl)-1H-pyrrole-2-carboxamide,
5. N-(6-(4-isopropyl-4H-1,2,4-triazol-3-yl)pyridin-2-yl)-4-p-tolyl-1H-pyrrole-2-carboxamide,
6. N-(6-(4-isopropyl-4H-1,2,4-triazol-3-yl)pyridin-2-yl)-4-phenyl-1H-pyrrole-2-carboxamide,
7. N-(6-(4-isopropyl-4H-1,2,4-triazol-3-yl)pyridin-2-yl)-1H-pyrrole-2-carboxamide,
8. N-(6-(4-isopropyl-4H-1,2,4-triazol-3-yl)pyridin-2-yl)-5-methyl-1H-pyrrole-2-carboxamide,
9. N-(6-(4-isopropyl-4H-1,2,4-triazol-3-yl)pyridin-2-yl)-5-phenyl-1H-pyrrole-2-carboxamide,
10. N-(6-(4-isopropyl-4H-1,2,4-triazol-3-yl)pyridin-2-yl)-5-p-tolyl-1H-pyrrole-2-carboxamide,
11. 5-ethyl-N-(6-(4-isopropyl-4H-1,2,4-triazol-3-yl)pyridin-2-yl)-1H-pyrrole-2-carboxamide,
12. N-(6-(4-isopropyl-4H-1,2,4-triazol-3-yl)pyridin-2-yl)-5-(2-methylpyrimidine-5-yl)-1H-pyrrole-2-carboxamide,
13. N-(6-(4-isopropyl-4H-1,2,4-triazol-3-yl)pyridin-2-yl)-5-(4-(methylsulfonyl)phenyl)-1H-pyrrole-2-carboxamide,
14. N-(6-(4-isopropyl-4H-1,2,4-triazol-3-yl)pyridin-2-yl)-5-m-tolyl-1H-pyrrole-2-carboxamide,
15. 5-(3,5-dimethylphenyl)-N-(6-(4-isopropyl-4H-1,2,4-triazol-3-yl)pyridin-2-yl)-1H-pyrrole-2-carboxamide,
16. 5-(4-chlorophenyl)-N-(6-(4-isopropyl-4H-1,2,4-triazol-3-yl)pyridin-2-yl)-1H-pyrrole-2-carboxamide,
17. N-(6-(4-isopropyl-4H-1,2,4-triazol-3-yl)pyridin-2-yl)-5-(thiophene-2-yl)-1H-pyrrole-2-carboxamide,
18. 5-(3,4-dimethylphenyl)-N-(6-(4-isopropyl-4H-1,2,4-triazol-3-yl)pyridin-2-yl)-1H-pyrrole-2-carboxamide,
19. 5-(3-fluoro-4-methylphenyl)-N-(6-(4-isopropyl-4H-1,2,4-triazol-3-yl)pyridin-2-yl)-1H-pyrrole-2-carboxamide,
20. 5-(3-chloro-4-fluorophenyl)-N-(6-(4-isopropyl-4H-1,2,4-triazol-3-yl)pyridin-2-yl)-1H-pyrrole-2-carboxamide,
21. N-(6-(4-isopropyl-4H-1,2,4-triazol-3-yl)pyridin-2-yl)-5-(4-(methylthio)phenyl)-1H-pyrrole-2-carboxamide,
22. N-(6-(4-isopropyl-4H-1,2,4-triazol-3-yl)pyridin-2-yl)-5-o-tolyl-1H-pyrrole-2-carboxamide,
23. 5-(4-fluorophenyl)-N-(6-(4-isopropyl-4H-1,2,4-triazol-3-yl)pyridin-2-yl)-1H-pyrrole-2-carboxamide, or
24. 5-(4-ethoxyphenyl)-N-(6-(4-isopropyl-4H-1,2,4-triazol-3-yl)pyridin-2-yl)-1H-pyrrole-2-carboxamide, but is not limited thereto.

In addition, the compound of the present disclosure may exist in the form of a pharmaceutically acceptable salt. An acid-addition salt formed by a pharmaceutically acceptable free acid may be useful as the salt. As used herein, the term "pharmaceutically acceptable salt" refers to any organic or inorganic addition salt of the compound, which has a concentration such that it exhibits an effective action that is relatively nontoxic and harmless to patients and whose side effects caused by the salt do not impair the beneficial effect of the compound represented by Chemical Formula 1. The pharmaceutically acceptable salt may include an acid-addition salt formed by an acid that can form nontoxic acid-addition salt containing pharmaceutically acceptable anions, for example, inorganic acids such as hydrochloric acid, sulfuric acid, nitric acid, phosphoric acid, hydrobromic acid, hydroiodic acid and the like, organic carbonic acids such as tartaric acid, formic acid, citric acid, acetic acid, adipic acid, trichloroacetic acid, trifluoroacetic acid, gluconic acid, benzoic acid, lactic acid, fumaric acid, maleic acid and the like, or sulfonic acids such as methanesulfonic acid, benzenesulfonic acid, p-Toluenesulfonic acid or naphthalenesulfonic acid, and the like. The compound of Chemical Formula 1 according to the present disclosure can be converted into its salt by a conventional method.

The acid-addition salt may be prepared by a conventional method, for example, by dissolving a compound in an excessive amount of acid aqueous solution, followed by precipitating the salt using a water-miscible organic solvent such as methanol, ethanol, acetone or acetonitrile. An acid or alcohol (e.g., glycol monomethyl ether) in an equal molar amount of the compound and water may be heated, and subsequently, the mixture may be dried by evaporation, or the precipitated salt may be suction-filtered.

Further, a pharmaceutically acceptable metal salt may be prepared using a base. An alkali metal salt or an alkaline earth metal salt is obtained, for example, by dissolving a compound in an excessive amount of an alkali metal hydroxide or an alkaline earth metal hydroxide solution, followed by filtering undissolved compound salts, and evaporating and drying the filtrate.

The pharmaceutically acceptable salt of the compound of the present disclosure may include a salt of an acidic or a basic group, which can be present in the compound of Chemical Formula 1, unless otherwise specifically indicated, and may be prepared by a method of preparing salts known in the art.

In addition, the present disclosure is intended to include not only the compound of Chemical Formula 1 and a pharmaceutically acceptable salt thereof, but also possible solvates that may be prepared therefrom.

Further, since the compound of the present disclosure has an asymmetric carbon center in the parent structure and its substituent groups, it can exist as R- or S-isomers, racemic mixtures, diastereomers mixtures and individual diastereomers, and all of these isomers and mixtures thereof are within the scope of the present disclosure. That is, if the asymmetric carbon(s) is present in the structure of Chemical Formula 1, it is understood that all stereoisomers are included within the scope of the present disclosure, as long as the direction is not described separately.

The compound represented by Chemical Formula 1 of the present disclosure may be prepared by a method including:
reacting a compound represented by Chemical Formula 2 below with 6-(4-isopropyl-4H-1,2,4-triazol-3-yl)pyridin-2-amine:

[Chemical Formula 2]

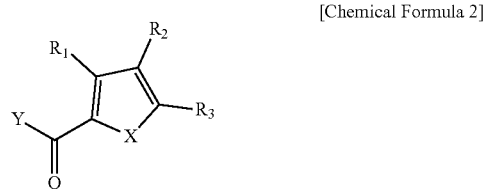

in the Chemical Formula 2,

X is NH, O or S,

Y is OH or halogen, and $R_1$ to $R_3$ are as defined above.

Specifically, if Y is OH, the above reaction may be performed in the presence of 1-[bis(dimethylamino)methylene]-1H-1,2,3-triazolo[4,5-b]pyridinium 3-oxide hexafluorophosphate (HATU) and a base, but is not limited thereto.

In particular, N-methylmorpholine may be used as the base, and N,N-dimethylformamide may be used as the solvent, but these are not limited thereto. Further, the reaction may be performed by adjusting the temperature to 90° C. to 110° C., but is not limited thereto.

Meanwhile, if Y is halogen, the reaction may be performed in the presence of triethylamine, but these are not limited thereto. In addition, the reaction may be performed by further adding a nucleophilic catalyst, and herein, 4-dimethylaminopyridine (DMAP) may be used as the nucleophilic catalyst, but these are not limited thereto.

For example, the reaction may be performed at room temperature, e.g., 10° C. to 35° C. using dichloromethane as a solvent, but is not limited thereto.

Specifically, the compound of Chemical Formula 2, wherein Y is halogen, may be prepared by a reaction of the compound of Chemical Formula 2, wherein Y is OH, i.e., a benzoic acid derivative compound, with oxalyl halide, but is not limited thereto.

For example, the reaction may be performed at room temperature, e.g., 10° C. to 35° C. using dichloromethane containing N,N-dimethylformamide as a solvent, but is not limited thereto.

More specifically, the compound of Chemical Formula 1 of the present disclosure may be prepared according to Reaction Scheme 1 or 2 below, using the compound of Chemical Formula 2, wherein Y is OH, i.e., a benzoic acid derivative compound, as a starting material.

[Reaction Scheme 1]

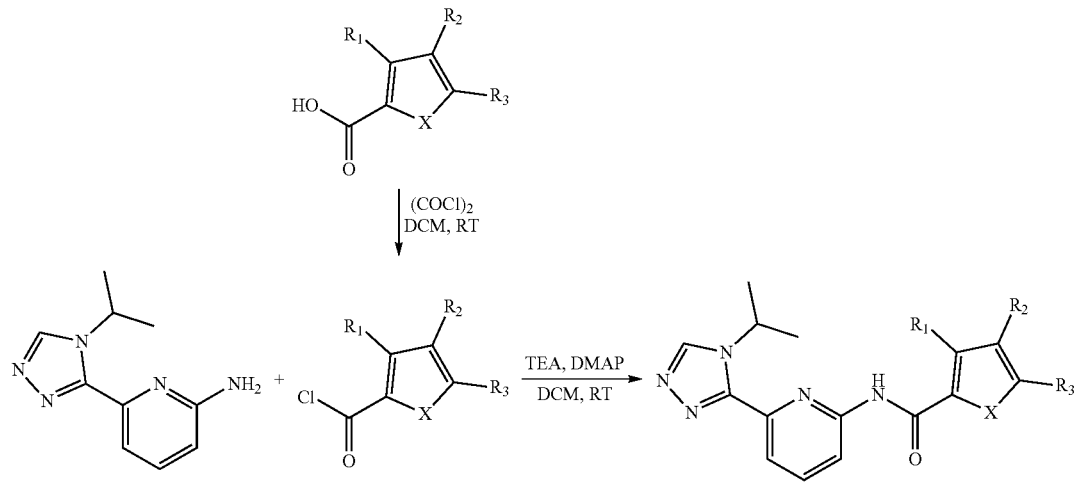

[Reaction Scheme 1]

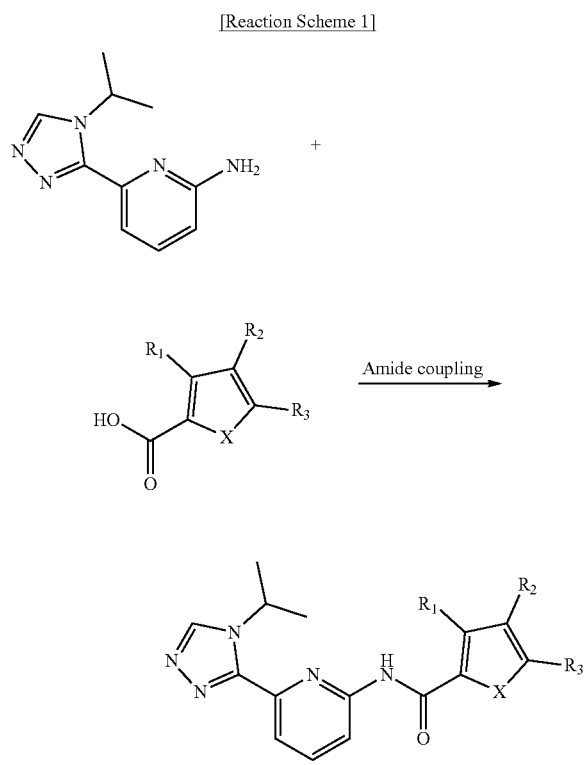

The type of Reaction Scheme used herein may be selected according to the position of the substituent of the target compound to be finally synthesized. For example, Reaction Scheme 1 may be selected when preparing a compound, wherein $R_1$ and $R_3$ are both hydrogen, and $R_2$ is any substituent other than hydrogen, whereas Reaction Scheme 2 may be selected when preparing a compound, wherein $R_1$ and $R_2$ are both hydrogen, and $R_3$ is any substituent other than hydrogen, but is not limited thereto.

For example, after completion of each reaction, a separation and/or purification process may be further carried out in order to improve the efficiency of the reaction, or to increase the purity of the product. The separation and purification process can be carried out using any method known in the art without limitation.

Meanwhile, the above-described series of Reaction Schemes are merely provided for illustration of the preparation method of the compound of the present disclosure, and the preparation method of the compound of the present disclosure is not limited thereto, and may be carried out using methods known in the art or with appropriate modifications.

In addition, the present disclosure provides a pharmaceutical composition for preventing or treating an ASK-1 mediated disease, including the compound represented by Chemical Formula 1 or a pharmaceutically acceptable salt thereof as an active ingredient.

Further, the present disclosure provides a method for preventing or treating an ASK-1 mediated disease, including administering the pharmaceutical composition to a subject in need thereof.

Specifically, the compound of the present disclosure or a pharmaceutically acceptable salt thereof has a feature of inhibiting ASK-1 activity.

As used herein, the term "preventing" or "prevention" refers to all actions that suppress or delay the onset, spread and recurrence of the ASK-1 mediated diseases by the administration of the pharmaceutical composition. In addition, the term "treating" or "treatment" refers to all actions that alleviate or beneficially change the symptoms of the above disease by the administration of the pharmaceutical composition.

For example, the pharmaceutical composition according to the present disclosure may contain the compound represented by Chemical Formula 1 or a pharmaceutically acceptable salt thereof as an active ingredient in an amount of 0.1% to 75% by weight, specifically 1% to 50% by weight, based on the total weight of the composition.

The ASK-1 mediated diseases, which can be prevented or treated by administration of the pharmaceutical composition including the compound of Chemical Formula 1 according to the present disclosure may include diabetes, diabetic nephropathy, kidney disease, kidney fibrosis, lung fibrosis, idiopathic pulmonary fibrosis (IPF), liver fibrosis, pulmonary hypertension, chronic obstructive pulmonary disease (COPD), acute lung injury, nonalcoholic steatohepatitis, liver disease, alcoholic liver disease, alcoholic hepatitis, inflammatory condition, autoimmune disease, proliferative disease, transplantation rejection, a disease accompanying impairment of cartilage turnover, congenital cartilage malformation, or a disease associated with hypersecretion of IL6, but the disease is not limited thereto.

In a specific embodiment of the present disclosure, it was confirmed that the ASK-1 activity could be effectively inhibited by the administration of the compound of Chemical Formula 1 according to the present disclosure. Based on this finding, it was found that the compound of Chemical Formula 1 according to the present disclosure can be used for the prevention or treatment of diseases caused by ASK-1 activation.

As used herein, the term "subject" refers to all animals including monkeys, cattle, horses, sheep, pigs, chickens, turkeys, quails, cats, dogs, mice, rats, rabbits, or guinea pigs, as well as humans having the ASK-1 mediated disease or being at risk of having the same, and the disease may be effectively prevented or treated by administering the pharmaceutical composition of the present disclosure to the subject. The pharmaceutical composition of the present disclosure may be administered in combination with a conventional therapeutic agent.

As used herein, the term "administration" refers to the introduction of a predetermined substance to a patient by any appropriate method. The composition of the present disclosure may be administered via any common route as long as it can reach a desired tissue. The composition may be administered via an intraperitoneal route, an intravenous route, an intramuscular route, a subcutaneous route, an intradermal route, an oral route, a topical route, an intranasal route, an intrapulmonary route or an intrarectal route, but is not limited thereto. In addition, the pharmaceutical composition may be administered by any device capable of delivering the active component to the target cell.

The pharmaceutical composition according to the present disclosure may contain the compound represented by Chemical Formula 1 or a pharmaceutically acceptable salt thereof as an active ingredient, and may further include a pharmaceutically acceptable carrier, diluent, or excipient. As used herein, the term "pharmaceutically acceptable carrier or diluent" refers to a carrier or diluent which neither causes significant stimulation to an organism nor abolishes the biological activities or properties of a compound to be administered thereto. In addition, as used herein, the term "pharmaceutically acceptable excipient" refers to an inert material which is added to the pharmaceutical composition to facilitate the administration of the compound represented by Chemical Formula 1 of the present disclosure. Examples of the excipient may include calcium carbonate, calcium phosphate, various types of sugars and starches, cellulose derivatives, gelatin, vegetable oil, and polyethylene glycol, but are not limited thereto. Further, the composition may be prepared into various formulations including oral for-mulation such as powders, granules, tablets, capsules, suspensions, emulsions, syrups, aerosols, and the like, and injection of sterile injectable solution, and the like, according to conventional methods depending on the desired purpose.

The pharmaceutical composition of the present disclosure may be administered in a pharmaceutically effective amount or a therapeutically effective amount. As used herein, the term "pharmaceutically effective amount" refers to an amount sufficient to treat a disease at a reasonable benefit/risk ratio applicable to any medical treatment without causing an adverse effect, and the effective dosage level may be determined based on the factors including the heath condition of a patient, the type and severity of a disease, the activity of a drug, the sensitivity to a drug, an administration method, an administration time, an administration route and an excretion rate, a duration of treatment, drugs used simultaneously or in combination, and other factors well known in the medical field. In view of all the above elements, it is important to administer the composition at a dose at which the maximum effect can be achieved with the minimum amount without adverse effects. Thus, the dose of the composition may be easily determined by those skilled in the art. The daily dosage of the compound represented by Chemical Formula 1 or a pharmaceutically acceptable salt thereof may be specifically 1 mg/kg to 1000 mg/kg, and the composition may be administered once daily or several times a day as needed.

MODE FOR THE INVENTION

Hereinafter, preferred Examples are provided to help understanding of the present disclosure. However, these Examples are given for illustrative purposes only to help better understanding of the present disclosure, and the scope of the present disclosure is not intended to be limited to or by these Examples.

Various synthesis methods of starting materials for synthesizing the compound of the present disclosure have been known, and the starting materials may be purchased from the suppliers, if available on the market. Examples of the reagent suppliers include Sigma-Aldrich, TCI, Wako, Kanto, Fluorchem, Acros, Alfa, Fluka, Dae-Jung, Combi-Blocks, etc., but are not limited thereto. Further, all the commercially available materials were used without further purification unless specified otherwise.

First, the compounds used for syntheses in Examples were prepared according to Preparation Examples below. Preparation Examples are exemplary embodiments of the compound represented by Chemical Formula 1 in Reaction Scheme 1 above, and may be appropriately adjusted corresponding to the structures of the compounds in the Examples to be prepared.

Preparation Example 1: Preparation of N-(6-(4-isopropyl-4H-1,2,4-triazol-3-yl)pyridin-2-yl)-4-methyl-1H-pyrrole-2-carboxamide Step 1-1) Preparation of 4-methyl-1H-pyrrole-2-carbonyl chloride

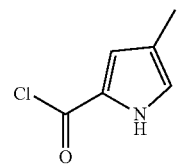

4-Methyl-1H-pyrrole-2-carboxylic acid (200 mg, 1.60 mmol) was dissolved in 3 mL of dichloromethane and 0.1 mL of N,N-dimethylformamide, and oxalyl chloride (0.18 mL, 2.08 mmol) was slowly added dropwise thereto. The mixture was stirred for 1 hour at room temperature to synthesize 4-methyl-1H-pyrrole-2-carbonyl chloride.

Step 1-2) Preparation of N-(6-(4-isopropyl-4H-1,2,4-triazol-3-yl)pyridin-2-yl)-4-methyl-1H-pyrrole-2-carboxamide

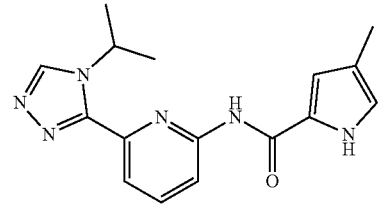 [SMILES: Cc1c[nH]c(C(=O)Nc2cccc(-c3nncn3C(C)C)n2)c1]

The reaction solution containing 4-methyl-1H-pyrrole-2-carbonyl chloride synthesized according to Step 1-1) above was concentrated under reduced pressure and then dissolved again in 3 mL of dichloromethane. To the reaction solution, 6-(4-isopropyl-4H-1,2,4-triazol-3-yl)pyridin-2-amine (360 mg, 1.76 mmol) was added, and triethylamine (0.29 mL, 2.08 mmol) was slowly added dropwise, and then the reaction solution was stirred at room temperature for 16 hours. After concentrating the reaction solution under reduced pressure, 6 mL of a 1:1 mixed solution of acetonitrile and distilled water was added thereto to obtain 100 mg of the title compound N-(6-(4-isopropyl-4H-1,2,4-triazol-3-yl)pyridin-2-yl)-4-methyl-1H-pyrrole-2-carboxamide.

$^1$H NMR (400 MHz, DMSO-d$_6$) δ 11.54 (br s, 1H), 10.07 (s, 1H), 8.87 (s, 1H), 8.17 (d, J=8.6 Hz, 1H), 7.96 (t, J=8.0 Hz, 1H), 7.77 (d, J=7.7 Hz, 1H), 7.01 (br s, 1H), 6.82 (br s, 1H), 5.65 (br d, J=6.6 Hz, 1H), 2.07 (s, 3H), 1.44 (d, J=6.8 Hz, 6H);

MS(ESI+) m/z 311 (M+H)$^+$.

Preparation Example 2: Preparation of N-(6-(4-isopropyl-4H-1,2,4-triazol-3-yl)pyridin-2-yl)-1H-pyrrole-2-carboxamide

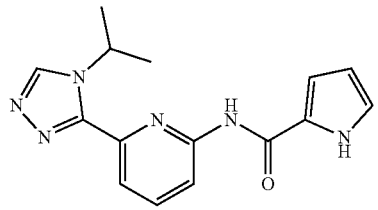

6-(4-Isopropyl-4H-1,2,4-triazol-3-yl)pyridin-2-amine (100 mg, 0.492 mmol) was dissolved in 2 mL of N,N-dimethylformamide, and 1H-pyrrole-2-carboxylic acid (66 mg, 0.590 mmol), 1-[bis(dimethylamino)methylene]-1H-1,2,3-triazolo[4,5-b]pyridinium 3-oxide hexafluorophosphate (HATU, 225 mg, 0.590 mmol) and N-methylmorpholine (162 μL, 1.476 mmol) were added thereto, and the mixture was stirred at 100° C. for 12 hours. After completion of the reaction, the mixture was cooled to room temperature and extracted with saturated aqueous ammonium chloride solution and ethyl acetate. The extracted solution was dried over anhydrous magnesium sulfate, filtered and concentrated under reduced pressure. The residue was separated by prep. TLC (dichloromethane:methanol=15:1) to obtain 11 mg of the title compound N-(6-(4-isopropyl-4H-1,2,4-triazol-3-yl)pyridin-2-yl)-1H-pyrrole-2-carboxamide.

$^1$H NMR (400 MHz, CDCl$_3$) δ 9.82 (s, 1H), 8.37 (s, 1H), 8.33 (d, J=1.2 Hz, 1H), 8.32 (s, 1H), 7.92-7.84 (m, 2H), 7.18-7.04 (m, 1H), 6.94 (s, 1H), 6.35-6.33 (m, 1H), 5.48-5.40 (m, 1H), 1.59 (d, J=1.0 Hz, 6H);

MS(ESI+) m/z 297 (M+H)$^+$.

Example 1: Preparation of N-(6-(4-isopropyl-4H-1,2,4-triazol-3-yl)pyridin-2-yl)-4-methyl-1H-pyrrole-2-carboxamide

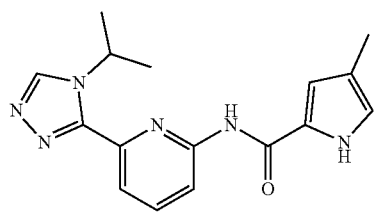 [SMILES: Cc1c[nH]c(C(=O)Nc2cccc(-c3nncn3C(C)C)n2)c1]

The above compound was obtained in the same manner as in Preparation Example 1.

$^1$H NMR (400 MHz, DMSO-d$_6$) δ 11.54 (br s, 1H), 10.07 (s, 1H), 8.87 (s, 1H), 8.17 (d, J=8.6 Hz, 1H), 7.96 (t, J=8.0 Hz, 1H), 7.77 (d, J=7.7 Hz, 1H), 7.01 (br s, 1H), 6.82 (br s, 1H), 5.65 (br d, J=6.6 Hz, 1H), 2.07 (s, 3H), 1.44 (d, J=6.8 Hz, 6H);

MS(ESI+) m/z 311 (M+H)$^+$.

Example 2: Preparation of N-(6-(4-isopropyl-4H-1,2,4-triazol-3-yl)pyridin-2-yl)-4-m-tolyl-1H-pyrrole-2-carboxamide

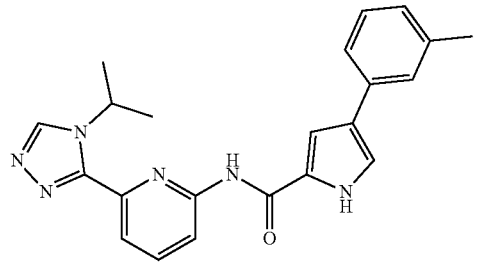 [SMILES: Cc1cccc(-c2c[nH]c(C(=O)Nc3cccc(-c4nncn4C(C)C)n3)c2)c1]

The above compound was obtained in the same manner as in Preparation Example 1.

$^1$H NMR (400 MHz, DMSO-d$_6$) δ 12.03-12.11 (m, 1H), 10.28-10.34 (m, 1H), 8.89 (s, 1H), 8.20 (br d, J=8.2 Hz, 1H), 7.97-8.03 (m, 1H), 7.77-7.81 (m, 1H), 7.59-7.65 (m, 2H), 7.53-7.57 (m, 1H), 7.33-7.39 (m, 2H), 7.16-7.21 (m, 1H), 5.61-5.67 (m, 1H), 2.16-2.32 (m, 3H), 1.41-1.51 (m, 6H);

MS(ESI+) m/z 387 (M+H)$^+$.

Example 3: Preparation of N-(6-(4-isopropyl-4H-1,2,4-triazol-3-yl)pyridin-2-yl)-4-(methoxymethyl)-1H-pyrrole-2-carboxamide

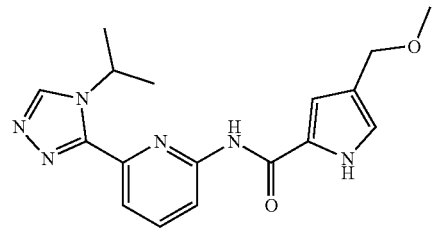 [SMILES: COCc1c[nH]c(C(=O)Nc2cccc(-c3nncn3C(C)C)n2)c1]

The above compound was obtained in the same manner as in Preparation Example 1.

$^1$H NMR (400 MHz, DMSO-d$_6$) δ 11.78 (br s, 1H), 10.18 (s, 1H), 8.86 (s, 1H), 8.16 (d, J=8.2 Hz, 1H), 7.97 (t, J=8.1 Hz, 1H), 7.79 (d, J=7.5 Hz, 1H), 7.20 (s, 1H), 7.01 (s, 1H), 5.63-5.74 (m, 1H), 4.28 (s, 2H), 3.23 (s, 3H), 1.45 (d, J=6.8 Hz, 6H);

MS(ESI+) m/z 341 (M+H)$^+$.

Example 4: Preparation of 4-ethyl-N-(6-(4-isopropyl-4H-1,2,4-triazol-3-yl)pyridin-2-yl)-1H-pyrrole-2-carboxamide

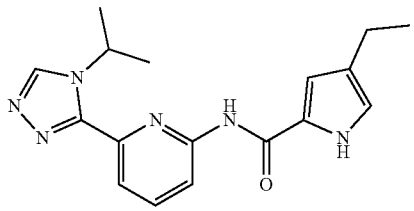 [SMILES: CCc1c[nH]c(C(=O)Nc2cccc(-c3nncn3C(C)C)n2)c1]

The above compound was obtained in the same manner as in Preparation Example 1.

$^1$H NMR (400 MHz, DMSO-d$_6$) δ 11.49-11.62 (m, 1H), 10.08 (br s, 1H), 8.86 (s, 1H), 8.16 (d, J=8.2 Hz, 1H), 7.93-8.03 (m, 1H), 7.76 (d, J=7.7 Hz, 1H), 7.05 (s, 1H), 6.84 (s, 1H), 5.60-5.70 (m, 1H), 2.55 (br d, J=3.1 Hz, 1H), 2.39-2.48 (m, 2H), 1.44 (d, J=6.6 Hz, 6H), 1.16 (t, J=7.6 Hz, 3H);

MS(ESI+) m/z 325 (M+H)$^+$.

Example 5: Preparation of N-(6-(4-isopropyl-4H-1,2,4-triazol-3-yl)pyridin-2-yl)-4-p-tolyl-1H-pyrrole-2-carboxamide

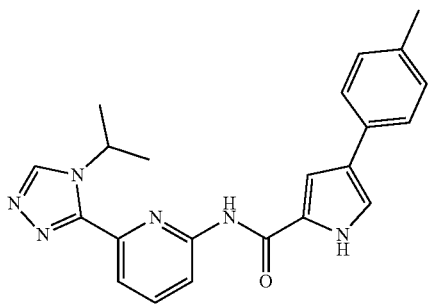 [SMILES: Cc1ccc(-c2c[nH]c(C(=O)Nc3cccc(-c4nncn4C(C)C)n3)c2)cc1]

The above compound was obtained in the same manner as in Preparation Example 1.

$^1$H NMR (400 MHz, DMSO-d$_6$) δ 11.97-12.08 (m, 1H), 10.28 (br s, 1H), 8.88 (s, 1H), 8.19 (br d, J=8.4 Hz, 1H), 7.99 (br t, J=8.1 Hz, 1H), 7.78 (br d, J=7.3 Hz, 1H), 7.43-7.64 (m, 3H), 7.09-7.25 (m, 2H), 5.85-5.98 (m, 1H), 5.60-5.71 (m, 1H), 2.16-2.32 (m, 3H), 1.31-1.64 (m, 6H);

MS(ESI+) m/z 387 (M+H)$^+$.

Example 6: Preparation of N-(6-(4-isopropyl-4H-1,2,4-triazol-3-yl)pyridin-2-yl)-4-phenyl-1H-pyrrole-2-carboxamide

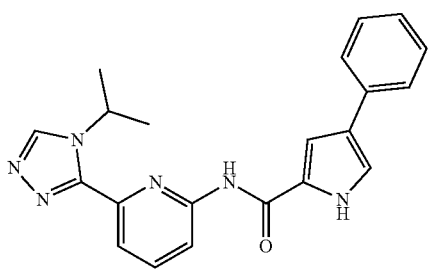 [SMILES: CC(C)n1cnnc1-c1cccc(NC(=O)c2cc(-c3ccccc3)c[nH]2)n1]

The above compound was obtained in the same manner as in Preparation Example 1.

$^1$H NMR (400 MHz, DMSO-d$_6$) δ 12.03-12.11 (m, 1H), 10.28-10.34 (m, 1H), 8.89 (s, 1H), 8.20 (br d, J=8.2 Hz, 1H), 7.97-8.03 (m, 1H), 7.77-7.81 (m, 1H), 7.59-7.65 (m, 3H), 7.53-7.57 (m, 1H), 7.33-7.39 (m, 2H), 7.16-7.21 (m, 1H), 5.61-5.67 (m, 1H), 1.41-1.51 (m, 6H);

MS(ESI+) m/z 373 (M+H)$^+$.

Example 7: Preparation of N-(6-(4-isopropyl-4H-1,2,4-triazol-3-yl)pyridin-2-yl)-1H-pyrrole-2-carboxamide

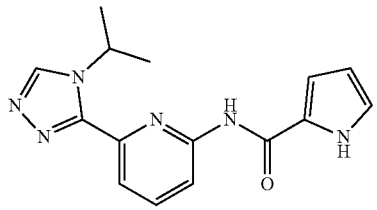 [SMILES: CC(C)n1cnnc1-c1cccc(NC(=O)c2ccc[nH]2)n1]

The above compound was obtained in the same manner as in Preparation Example 2.

$^1$H NMR (400 MHz, CDCl$_3$) δ 9.82 (s, 1H), 8.37 (s, 1H), 8.33 (d, J=1.2 Hz, 1H), 8.32 (s, 1H), 7.92-7.84 (m, 2H), 7.18-7.04 (m, 1H), 6.94 (s, 1H), 6.35-6.33 (m, 1H), 5.48-5.40 (m, 1H), 1.59 (d, J=1.0 Hz, 6H);

MS(ESI+) m/z 297 (M+H)$^+$.

Example 8: Preparation of N-(6-(4-isopropyl-4H-1,2,4-triazol-3-yl)pyridin-2-yl)-5-methyl-1H-pyrrole-2-carboxamide

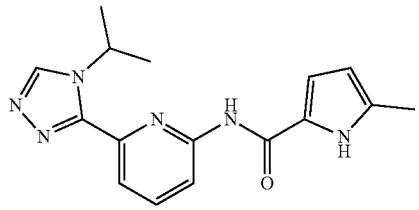 [SMILES: Cc1ccc(C(=O)Nc2cccc(-c3nncn3C(C)C)n2)[nH]1]

The above compound was obtained in the same manner as in Preparation Example 2.

$^1$H NMR (400 MHz, CDCl$_3$) δ 9.54 (s, 1H), 8.37 (s, 1H), 8.32 (d, J=8.0 Hz, 1H), 8.11 (s, 1H), 7.92-7.83 (m, 2H), 6.74-6.73 (m, 1H), 5.99-5.98 (m, 1H), 5.49-5.42 (m, 1H), 2.36 (s, 3H), 1.55 (d, J=6.8 Hz, 6H);

MS(ESI+) m/z 311 (M+H)$^+$.

Example 9: Preparation of N-(6-(4-isopropyl-4H-1,2,4-triazol-3-yl)pyridin-2-yl)-5-phenyl-1H-pyrrole-2-carboxamide

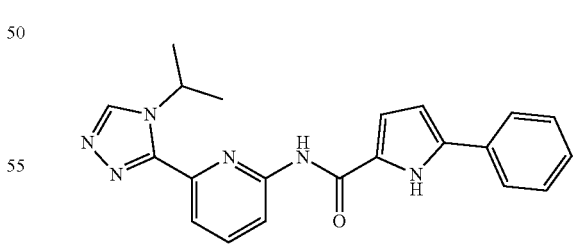

The above compound was obtained in the same manner as in Preparation Example 2.

$^1$H NMR (400 MHz, CDCl$_3$) δ 10.58 (s, 1H), 8.59 (s, 1H), 8.37 (s, 1H), 8.25 (d, J=8.2 Hz, 1H), 7.82 (d, J=7.6 Hz, 1H), 7.74-7.62 (m, 3H), 7.50-7.34 (m, 2H), 7.30-7.28 (m, 1H), 7.06-7.04 (m, 1H), 6.63-6.62 (m, 1H), 5.40-5.32 (m, 1H), 1.44 (d, J=6.6 Hz, 6H);

MS(ESI+) m/z 373 (M+H)$^+$.

Example 10: Preparation of N-(6-(4-isopropyl-4H-1,2,4-triazol-3-yl)pyridin-2-yl)-5-p-tolyl-1H-pyrrole-2-carboxamide

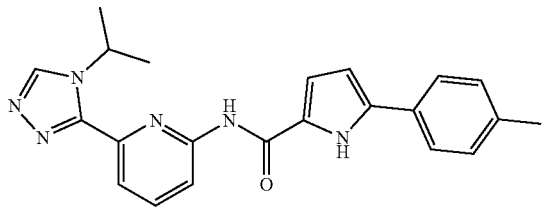 [SMILES: Cc1ccc(-c2ccc(C(=O)Nc3cccc(-c4nncn4C(C)C)n3)[nH]2)cc1]

The above compound was obtained in the same manner as in Preparation Example 2.

$^1$H NMR (400 MHz, CDCl$_3$) δ 10.32 (s, 1H), 8.44 (s, 1H), 8.39 (s, 1H), 8.27 (d, J=8.2 Hz, 1H), 7.85 (d, J=7.3 Hz, 1H), 7.77 (t, J=7.3 Hz, 1H), 7.64 (d, J=7.7 Hz, 2H), 7.19 (d, J=8.0 Hz, 2H), 7.06-6.99 (m, 1H), 6.63-6.59 (m, 1H), 5.48-5.37 (m, 1H), 2.34 (s, 3H), 1.50 (d, J=6.8 Hz, 6H);

MS(ESI+) m/z 387 (M+H)$^+$.

Example 11: Preparation of 5-ethyl-N-(6-(4-isopropyl-4H-1,2,4-triazol-3-yl)pyridin-2-yl)-1H-pyrrole-2-carboxamide

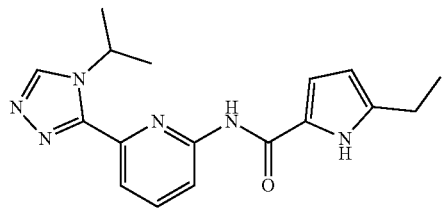 [SMILES: CCc1ccc(C(=O)Nc2cccc(-c3nncn3C(C)C)n2)[nH]1]

The above compound was obtained in the same manner as in Preparation Example 2.

$^1$H NMR (400 MHz, CDCl$_3$) δ 9.38 (s, 1H), 8.38 (s, 1H), 8.33 (d, J=8.2 Hz, 1H), 8.17 (s, 1H), 7.92-7.73 (m, 2H), 6.73-6.71 (m, 1H), 6.06-6.04 (m, 1H), 5.50-5.42 (m, 1H), 2.74-2.65 (m, 2H), 1.57 (d, J=6.8 Hz, 6H), 1.29 (t, J=8.0 Hz, 3H);

MS(ESI+) m/z 325 (M+H)$^+$.

Example 12: Preparation of N-(6-(4-isopropyl-4H-1,2,4-triazol-3-yl)pyridin-2-yl)-5-(2-methylpyrimidine-5-yl)-1H-pyrrole-2-carboxamide

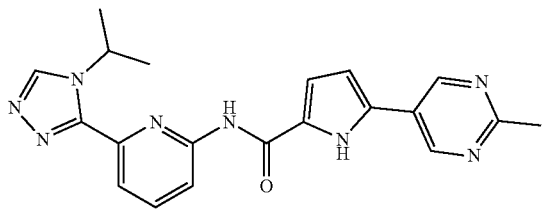 [SMILES: Cc1ncc(-c2ccc(C(=O)Nc3cccc(-c4nncn4C(C)C)n3)[nH]2)cn1]

The above compound was obtained in the same manner as in Preparation Example 2.

$^1$H NMR (400 MHz, CDCl$_3$) δ 8.96 (s, 2H), 8.38 (s, 1H), 8.29 (d, J=7.5 Hz, 1H), 7.85-7.74 (m, 2H), 7.01 (d, J=4.0 Hz, 1H), 6.66 (d, J=3.6, 1H), 5.37-5.34 (m, 1H), 2.74 (s, 3H), 1.50 (d, J=6.8 Hz, 6H);

MS(ESI+) m/z 389 (M+H)$^+$.

Example 13: Preparation of N-(6-(4-isopropyl-4H-1,2,4-triazol-3-yl)pyridin-2-yl)-5-(4-(methylsulfonyl)phenyl)-1H-pyrrole-2-carboxamide

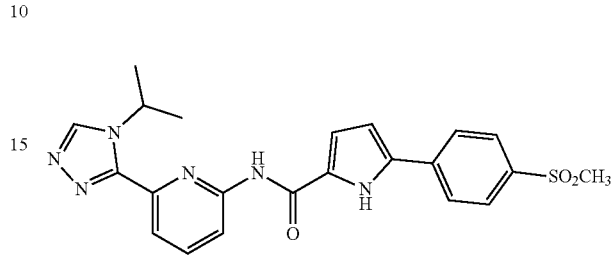

The above compound was obtained in the same manner as in Preparation Example 2.

$^1$H NMR (400 MHz, CDCl$_3$) δ 8.46 (s, 1H), 8.23 (d, J=6.8 Hz, 1H), 7.90-7.83 (m, 2H), 7.80-7.75 (m, 3H), 7.71 (d, J=7.5 Hz, 1H), 6.89 (d, J=4.0 Hz, 1H), 6.68 (d, J=4.0, 1H), 5.41-5.32 (m, 1H), 3.03 (s, 3H), 1.45 (d, J=6.8 Hz, 6H);

MS(ESI+) m/z 451 (M+H)$^+$.

Example 14: Preparation of N-(6-(4-isopropyl-4H-1,2,4-triazol-3-yl)pyridin-2-yl)-5-m-tolyl-1H-pyrrole-2-carboxamide

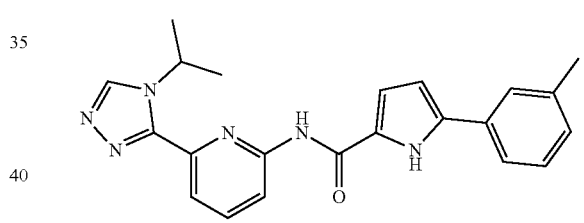

The above compound was obtained in the same manner as in Preparation Example 2.

$^1$H NMR (400 MHz, CDCl$_3$) δ 8.61 (s, 1H), 8.37 (s, 1H), 8.23 (d, J=7.3 Hz, 1H), 7.80 (d, J=6.8 Hz, 1H), 7.68 (t, J=6.8 Hz, 1H), 7.52-7.46 (m, 2H), 7.27-7.20 (m, 1H), 7.12-7.01 (m, 2H), 6.61-6.54 (m, 1H), 5.40-5.31 (m, 1H), 2.38 (s, 3H), 1.49 (d, J=6.8 Hz, 6H);

MS(ESI+) m/z 387 (M+H)$^+$.

Example 15: Preparation of 5-(3,5-dimethylphenyl)-N-(6-(4-isopropyl-4H-1,2,4-triazol-3-yl)pyridin-2-yl)-1H-pyrrole-2-carboxamide

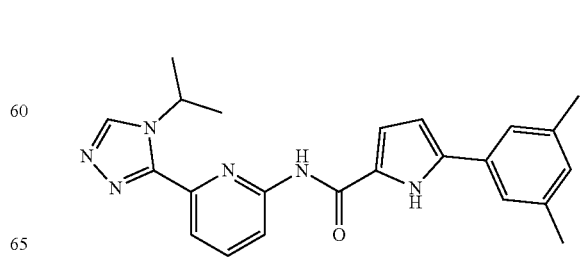

The above compound was obtained in the same manner as in Preparation Example 2.

¹H NMR (400 MHz, CDCl₃) δ 10.45 (s, 1H), 8.52 (s, 1H), 8.36 (s, 1H), 8.25 (d, J=6.6 Hz, 1H), 7.83-7.69 (m, 2H), 7.28 (s, 2H), 7.01 (s, 1H), 6.94 (s, 1H), 6.60-6.58 (m, 1H), 5.40-5.30 (m, 1H), 2.32 (s, 6H), 1.48 (d, J=7.6 Hz, 6H);

MS(ESI+) m/z 401 (M+H)⁺.

Example 16: Preparation of 5-(4-chlorophenyl)-N-(6-(4-isopropyl-4H-1,2,4-triazol-3-yl)pyridin-2-yl)-1H-pyrrole-2-carboxamide

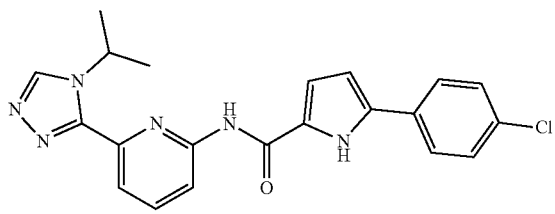 [SMILES: CC(C)n1cnnc1-c1cccc(NC(=O)c2ccc(-c3ccc(Cl)cc3)[nH]2)n1]

The above compound was obtained in the same manner as in Preparation Example 2.

¹H NMR (400 MHz, MeOD) δ 8.80 (s, 1H), 8.26 (d, J=6.8 Hz, 1H), 7.93-7.84 (m, 1H), 7.72 (d, J=6.8 Hz, 1H), 7.65 (d, J=4.0 Hz, 2H), 7.37 (d, J=4.0 Hz, 2H), 7.15-7.12 (m, 1H), 6.62-6.58 (m, 1H), 5.78-5.72 (m, 1H), 1.51 (d, J=8.0 Hz, 6H);

MS(ESI+) m/z 407 (M+H)⁺.

Example 17: Preparation of N-(6-(4-isopropyl-4H-1,2,4-triazol-3-yl)pyridin-2-yl)-5-(thiophene-2-yl)-1H-pyrrole-2-carboxamide

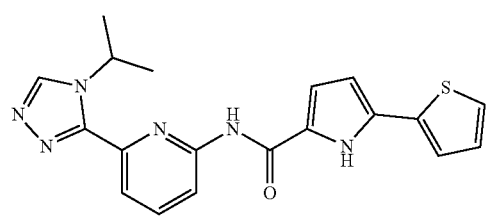 [SMILES: CC(C)n1cnnc1-c1cccc(NC(=O)c2ccc(-c3cccs3)[nH]2)n1]

The above compound was obtained in the same manner as in Preparation Example 2.

¹H NMR (400 MHz, CDCl₃) δ 10.87 (s, 1H), 8.71 (s, 1H), 8.36 (s, 1H), 8.20 (d, J=8.2 Hz, 1H), 7.79-7.62 (m, 2H), 7.38-7.32 (m, 1H), 7.20-7.16 (m, 1H), 7.06-7.01 (m, 1H), 6.79-6.49 (m, 1H), 5.32-5.23 (m, 1H), 1.51 (d, J=6.8 Hz, 6H);

MS(ESI+) m/z 379 (M+H)⁺.

Example 18: Preparation of 5-(3,4-dimethylphenyl)-N-(6-(4-isopropyl-4H-1,2,4-triazol-3-yl)pyridin-2-yl)-1H-pyrrole-2-carboxamide

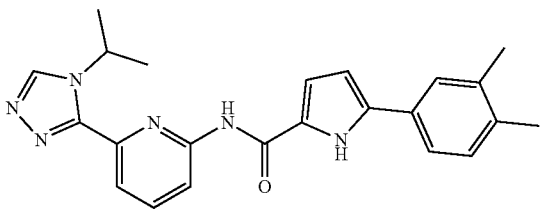 [SMILES: Cc1ccc(-c2ccc(C(=O)Nc3cccc(-c4nncn4C(C)C)n3)[nH]2)cc1C]

The above compound was obtained in the same manner as in Preparation Example 2.

¹H NMR (400 MHz, CDCl₃) δ 10.53 (s, 1H), 8.57 (s, 1H), 8.34 (s, 1H), 8.22 (d, J=8.2 Hz, 1H), 7.81 (d, J=7.3 Hz, 1H), 7.70-7.63 (m, 1H), 7.44-7.38 (m, 2H), 7.11 (d, J=8.2 Hz, 1H), 7.07-7.01 (m, 1H), 6.57-6.55 (m, 1H), 5.40-5.30 (m, 1H), 2.24 (s, 6H), 1.46 (d, J=6.8 Hz, 6H);

MS(ESI+) m/z 401 (M+H)⁺.

Example 19: Preparation of 5-(3-fluoro-4-methylphenyl)-N-(6-(4-isopropyl-4H-1,2,4-triazol-3-yl)pyridin-2-yl)-1H-pyrrole-2-carboxamide

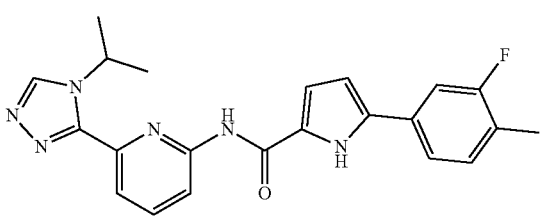 [SMILES: Cc1ccc(-c2ccc(C(=O)Nc3cccc(-c4nncn4C(C)C)n3)[nH]2)cc1F]

The above compound was obtained in the same manner as in Preparation Example 2.

¹H NMR (400 MHz, CDCl₃) δ 11.02 (s, 1H), 8.78 (s, 1H), 8.34 (s, 1H), 8.19 (d, J=6.6 Hz, 1H), 7.76-7.70 (m, 1H), 7.68-7.63 (m, 1H), 7.41-7.32 (m, 2H), 7.13-7.07 (m, 2H), 6.62-6.58 (m, 1H), 5.33-5.23 (m, 1H), 2.22 (s, 3H), 1.43 (d, J=6.8 Hz, 6H);

MS(ESI+) m/z 405 (M+H)⁺.

Example 20: Preparation of 5-(3-chloro-4-fluorophenyl)-N-(6-(4-isopropyl-4H-1,2,4-triazol-3-yl)pyridin-2-yl)-1H-pyrrole-2-carboxamide

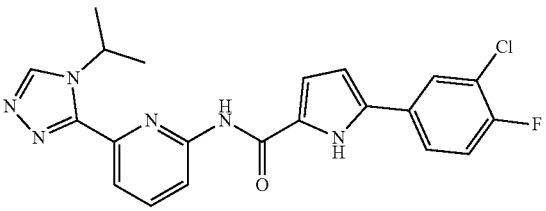 [SMILES: CC(C)n1cnnc1-c1cccc(NC(=O)c2ccc(-c3ccc(F)c(Cl)c3)[nH]2)n1]

The above compound was obtained in the same manner as in Preparation Example 2.

¹H NMR (400 MHz, CDCl₃) δ 11.05 (s, 1H), 8.79 (s, 1H), 8.38 (s, 1H), 8.16 (d, J=6.8 Hz, 1H), 7.81-7.64 (m, 3H), 7.60-7.54 (m, 1H), 7.17-7.09 (m, 2H), 6.60-6.56 (m, 1H), 5.24-5.17 (m, 1H), 1.48 (d, J=7.6 Hz, 6H);
MS(ESI+) m/z 425 (M+H)⁺.

Example 21: Preparation of N-(6-(4-isopropyl-4H-1,2,4-triazol-3-yl)pyridin-2-yl)-5-(4-(methylthio)phenyl)-1H-pyrrole-2-carboxamide

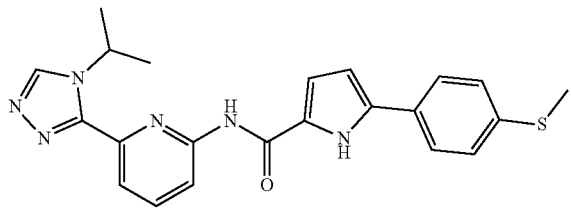 [SMILES: CSc1ccc(-c2ccc(C(=O)Nc3cccc(-c4nncn4C(C)C)n3)[nH]2)cc1]

The above compound was obtained in the same manner as in Preparation Example 2.
¹H NMR (400 MHz, CDCl₃) δ 10.57 (s, 1H), 8.56 (s, 1H), 8.35 (s, 1H), 8.22 (d, J=8.2 Hz, 1H), 7.81 (d, J=7.6 Hz, 1H), 7.73 (m, 1H), 7.57 (d, J=6.8 Hz, 2H), 7.24 (d, J=6.6 Hz, 2H), 7.02-7.00 (m, 1H), 6.59-6.57 (m, 1H), 5.35-5.30 (m, 1H), 2.46 (s, 3H), 1.47 (d, J=6.8 Hz, 6H);
MS(ESI+) m/z 419 (M+H)⁺.

Example 22: Preparation of N-(6-(4-isopropyl-4H-1,2,4-triazol-3-yl)pyridin-2-yl)-5-o-tolyl-1H-pyrrole-2-carboxamide

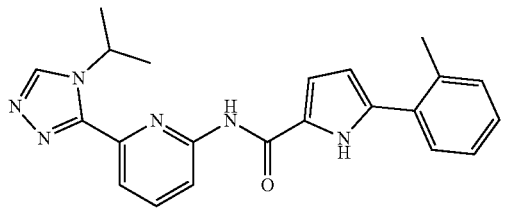 [SMILES: Cc1ccccc1-c1ccc(C(=O)Nc2cccc(-c3nncn3C(C)C)n2)[nH]1]

The above compound was obtained in the same manner as in Preparation Example 2.
¹H NMR (400 MHz, CDCl₃) δ 10.33 (s, 1H), 8.51 (s, 1H), 8.34 (s, 1H), 8.14 (d, J=4.0 Hz, 1H), 7.85 (d, J=6.6 Hz, 1H), 7.71 (t, J=6.8 Hz, 1H), 7.47-7.45 (m, 1H), 7.29-7.20 (m, 3H), 7.04-7.01 (m, 1H), 6.43-6.41 (m, 1H), 5.43-5.38 (m, 1H), 2.47 (s, 3H), 1.49 (d, J=6.8 Hz, 6H);
MS(ESI+) m/z 387 (M+H)⁺.

Example 23: Preparation of 5-(4-fluorophenyl)-N-(6-(4-isopropyl-4H-1,2,4-triazol-3-yl)pyridin-2-yl)-1H-pyrrole-2-carboxamide

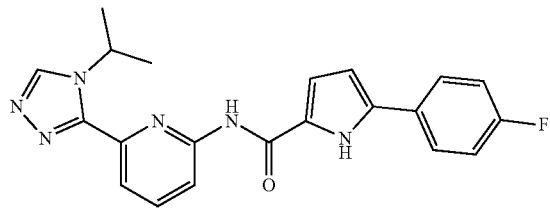 [SMILES: CC(C)n1cnnc1-c1cccc(NC(=O)c2ccc(-c3ccc(F)cc3)[nH]2)n1]

The above compound was obtained in the same manner as in Preparation Example 2.
¹H NMR (400 MHz, MeOD) δ 10.62 (s, 1H), 8.60 (s, 1H), 8.34 (s, 1H), 8.22 (d, J=6.8 Hz, 1H), 7.81-7.72 (m, 2H), 7.68-7.61 (m, 2H), 7.09-6.99 (m, 3H), 6.56-6.51 (m, 1H), 5.36-5.28 (m, 1H), 1.47 (d, J=8.0 Hz, 6H);
MS(ESI+) m/z 391 (M+H)⁺.

Example 24: Preparation of 5-(4-ethoxyphenyl)-N-(6-(4-isopropyl-4H-1,2,4-triazol-3-yl)pyridin-2-yl)-1H-pyrrole-2-carboxamide

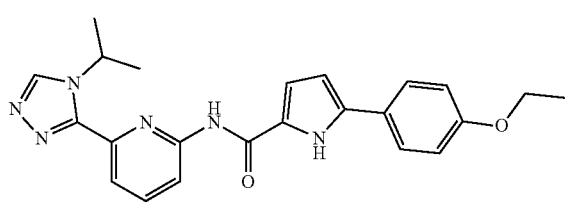 [SMILES: CCOc1ccc(-c2ccc(C(=O)Nc3cccc(-c4nncn4C(C)C)n3)[nH]2)cc1]

The above compound was obtained in the same manner as in Preparation Example 2.
¹H NMR (400 MHz, CDCl₃) δ 10.56 (s, 1H), 8.54 (s, 1H), 8.32 (s, 1H), 8.25 (d, J=8.0 Hz, 1H), 7.82-7.80 (m, 1H), 7.78-7.71 (m, 1H), 7.56 (d, J=6.6, 2H), 7.01 (s, 1H), 6.86 (d, J=8.8 Hz, 2H), 6.51 (s, 1H), 5.41-5.34 (m, 1H), 4.03-3.98 (m, 2H), 1.48 (d, J=6.8 Hz, 6H), 1.37 (t, J=8.0 Hz, 3H);
MS(ESI+) m/z 417 (M+H)⁺.

Experimental Example 1: Assay of Inhibitory Ability Against ASK-1 Enzyme Activity (ADP-Glo™ Kinase Assay)

In order to evaluate the inhibitory ability of the compounds of Examples 1 to 24 against ASK-1 enzyme activity, the following experiment was carried out using ADP-Glo™ (Promega, Cat. No. V9101). Each of the compounds was prepared into a solution at concentrations of 0.32 nM, 1.6 nM, 8 nM, 40 nM, 200 nM, 1,000 nM by adding a kinase buffer solution (40 mM Tris, 20 mM MgCl₂, 0.1 mg/mL bovine serum albumin in H₂O). Subsequently, 250 μM of ATP (Promega, Cat. No. V915A) and 0.5 μg/μL of MBP substrate (Signal Chem, Cat. No. 42-51N) were added thereto, and the mixture was reacted at 30° C. for 40 minutes in the presence of 15 ng of ASK-1 enzyme (Signal Chem, Cat. No. M13-11G-10). Then, the ADP-Glo™ reagent and a kinase detection reagent were sequentially added thereto and reacted for 40 minutes and 10 minutes, respectively. After completion of the reaction, luminescence was measured using a Synergy™ NEO microplate reader (BioTEK, NEOB-1311189).

The inhibitory ability of the compounds of Examples 1 to 24 against ASK-1 enzyme activity was verified by analyzing data from the measured RLU values. Specifically, the inhibitory ability against ASK-1 enzyme activity was assessed by deriving the residual activity percentage of the ASK-1 enzyme in the samples treated with the compounds at the concentration to be tested, while using the RLU value of the sample not treated with the compounds as a 100% control. The IC₅₀ value (nM) of the ASK-1 inhibitor was determined as the concentration of the compounds at which the inhibition of ASK-1 enzyme activity was induced by 50% compared to the control, and the results are shown in Table 1 below. As shown in Table 1, all of the compounds of Examples 1 to 24 showed excellent inhibitory activity against ASK-1 with the IC$_{50}$ values of 100 nM or below.

TABLE 11

| | ASK-1 IC$_{50}$ (nM) |
|---|---|
| Example 1 | 9.9 |
| Example 2 | 4.0 |
| Example 3 | 7.7 |
| Example 4 | 8.3 |
| Example 5 | 6.0 |
| Example 6 | 6.5 |
| Example 7 | 11.6 |
| Example 8 | 34.4 |
| Example 9 | 5.8 |
| Example 10 | 10.2 |
| Example 11 | 49.7 |
| Example 12 | 9.9 |
| Example 13 | 4.4 |
| Example 14 | 5.8 |
| Example 15 | 8.5 |
| Example 16 | 5.4 |
| Example 17 | 7.9 |
| Example 18 | 4.8 |
| Example 19 | 5.2 |
| Example 20 | 5.3 |
| Example 21 | 3.1 |
| Example 22 | 5.1 |
| Example 23 | 5.9 |
| Example 24 | 7.5 |

The invention claimed is:

1. A compound represented by Chemical Formula 1, or a pharmaceutically acceptable salt thereof:

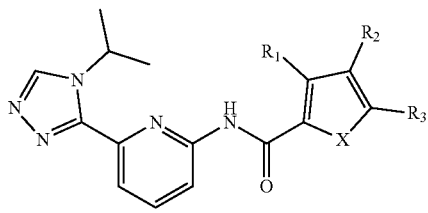

Chemical Formula 1 in which:
X is NH, O or S,
R$_1$ is hydrogen, C$_{1-6}$ alkyl, C$_{1-6}$ heteroalkyl, C$_{1-6}$ alkoxy, or halogen, and
R$_2$ and R$_3$ are each independently hydrogen, C$_{1-6}$ alkyl, C$_{1-6}$ heteroalkyl, C$_{1-6}$ alkoxy, halogen, cyano, nitro, amino, C$_{1-6}$ alkoxy-C$_{1-6}$ alkyl, C$_{6-10}$ aryl, C$_{6-10}$ arylamino, C$_{5-10}$ heteroaryl, or C$_{5-10}$ heteroarylamino,
wherein the aryl or heteroaryl is unsubstituted or substituted with at least one selected from the group consisting of C$_{1-6}$ alkyl, C$_{1-6}$ alkoxy, C$_{1-6}$ alkoxy-C$_{1-6}$ alkyl, halogen, nitro, cyano, amino, C$_{1-6}$ alkylamino, acetylamino, formyl, C$_{1-6}$ alkylcarbonyl, morpholinocarbonyl, morpholinyl, piperazinyl, piperidinyl, aminocarbonyl, C$_{1-6}$ alkylaminocarbonyl, di(C$_{1-6}$ alkyl)aminocarbonyl, C$_{1-6}$ alkyl-thio, cyano-C$_{1-6}$ alkyl, C$_{1-6}$ haloalkyl, C$_{1-6}$ dihaloalkyl, C$_{1-6}$ alkylsulfonyl, aminosulfonyl, C$_{1-6}$ alkylaminosulfonyl, di(C$_{1-6}$ alkyl)aminosulfonyl, C$_{1-6}$ heteroalkyl, and heteroaryl-C$_{1-6}$ alkyl.

2. The compound of claim 1 or a pharmaceutically acceptable salt thereof, wherein X is NH, and R$_1$ is hydrogen.

3. The compound of claim 1 or a pharmaceutically acceptable salt thereof, wherein R$_2$ and R$_3$ are each independently hydrogen, C$_{1-6}$ alkyl, C$_{1-6}$ alkoxy, C$_{1-6}$ alkoxy-C$_{1-6}$ alkyl, C$_{6-10}$ aryl, or C$_{5-10}$ heteroaryl.

4. The compound of claim 1 or a pharmaceutically acceptable salt thereof, wherein R$_2$ and R$_3$ are each independently hydrogen, methyl, ethyl, methoxymethyl, or unsubstituted or substituted phenyl, thiophenyl or pyrimidinyl.

5. The compound of claim 1 or a pharmaceutically acceptable salt thereof, wherein the aryl or heteroaryl is unsubstituted or substituted with at least one selected from the group consisting of methyl, chloro, fluoro, ethoxy, methylthio, and methylsulfonyl.

6. The compound of claim 1 or a pharmaceutically acceptable salt thereof, wherein the compound is
1. N-(6-(4-isopropyl-4H-1,2,4-triazol-3-yl)pyridin-2-yl)-4-methyl-1H-pyrrole-2-carboxamide,
2. N-(6-(4-isopropyl-4H-1,2,4-triazol-3-yl)pyridin-2-yl)-4-m-tolyl-1H-pyrrole-2-carboxamide,
3. N-(6-(4-isopropyl-4H-1,2,4-triazol-3-yl)pyridin-2-yl)-4-(methoxymethyl)-1H-pyrrole-2-carboxamide,
4. 4-ethyl-N-(6-(4-isopropyl-4H-1,2,4-triazol-3-yl)pyridin-2-yl)-1H-pyrrole-2-carboxamide,
5. N-(6-(4-isopropyl-4H-1,2,4-triazol-3-yl)pyridin-2-yl)-4-p-tolyl-1H-pyrrole-2-carboxamide,
6. N-(6-(4-isopropyl-4H-1,2,4-triazol-3-yl)pyridin-2-yl)-4-phenyl-1H-pyrrole-2-carboxamide,
7. N-(6-(4-isopropyl-4H-1,2,4-triazol-3-yl)pyridin-2-yl)-1H-pyrrole-2-carboxamide,
8. N-(6-(4-isopropyl-4H-1,2,4-triazol-3-yl)pyridin-2-yl)-5-methyl-1H-pyrrole-2-carboxamide,
9. N-(6-(4-isopropyl-4H-1,2,4-triazol-3-yl)pyridin-2-yl)-5-phenyl-1H-pyrrole-2-carboxamide,
10. N-(6-(4-isopropyl-4H-1,2,4-triazol-3-yl)pyridin-2-yl)-5-p-tolyl-1H-pyrrole-2-carboxamide,
11. 5-ethyl-N-(6-(4-isopropyl-4H-1,2,4-triazol-3-yl)pyridin-2-yl)-1H-pyrrole-2-carboxamide,
12. N-(6-(4-isopropyl-4H-1,2,4-triazol-3-yl)pyridin-2-yl)-5-(2-methylpyrimidine-5-yl)-1H-pyrrole-2-carboxamide,
13. N-(6-(4-isopropyl-4H-1,2,4-triazol-3-yl)pyridin-2-yl)-5-(4-(methylsulfonyl)phenyl)-1H-pyrrole-2-carboxamide,
14. N-(6-(4-isopropyl-4H-1,2,4-triazol-3-yl)pyridin-2-yl)-5-m-tolyl-1H-pyrrole-2-carboxamide,
15. 5-(3,5-dimethylphenyl)-N-(6-(4-isopropyl-4H-1,2,4-triazol-3-yl)pyridin-2-yl)-1H-pyrrole-2-carboxamide,
16. 5-(4-chlorophenyl)-N-(6-(4-isopropyl-4H-1,2,4-triazol-3-yl)pyridin-2-yl)-1H-pyrrole-2-carboxamide,
17. N-(6-(4-isopropyl-4H-1,2,4-triazol-3-yl)pyridin-2-yl)-5-(thiophene-2-yl)-1H-pyrrole-2-carboxamide,
18. 5-(3,4-dimethylphenyl)-N-(6-(4-isopropyl-4H-1,2,4-triazol-3-yl)pyridin-2-yl)-1H-pyrrole-2-carboxamide,
19. 5-(3-fluoro-4-methylphenyl)-N-(6-(4-isopropyl-4H-1,2,4-triazol-3-yl)pyridin-2-yl)-1H-pyrrole-2-carboxamide,
20. 5-(3-chloro-4-fluorophenyl)-N-(6-(4-isopropyl-4H-1,2,4-triazol-3-yl)pyridin-2-yl)-1H-pyrrole-2-carboxamide,
21. N-(6-(4-isopropyl-4H-1,2,4-triazol-3-yl)pyridin-2-yl)-5-(4-(methylthio)phenyl)-1H-pyrrole-2-carboxamide,
22. N-(6-(4-isopropyl-4H-1,2,4-triazol-3-yl)pyridin-2-yl)-5-o-tolyl-1H-pyrrole-2-carboxamide,
23. 5-(4-fluorophenyl)-N-(6-(4-isopropyl-4H-1,2,4-triazol-3-yl)pyridin-2-yl)-1H-pyrrole-2-carboxamide, or
24. 5-(4-ethoxyphenyl)-N-(6-(4-isopropyl-4H-1,2,4-triazol-3-yl)pyridin-2-yl)-1H-pyrrole-2-carboxamide.

7. A method for preparing the compound according to claim 1, comprising:
reacting a compound represented by Chemical Formula 2 with 6-(4-isopropyl-4H-1,2,4-triazol-3-yl)pyridin-2-amine, thereby forming the compound of Chemical Formula 1:

Chemical Formula 2

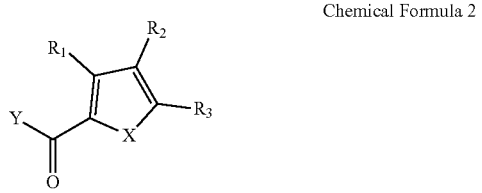

in which:
X is NH, O or S,
Y is OH or halogen, and
$R_1$ to $R_3$ are as defined in claim 1 above,
wherein, when Y is OH, the reaction is performed in the presence of 1-[bis(dimethylamino)methylene]-1H-1,2,3-triazolo[4,5-b]pyridinium 3-oxide hexafluorophosphate (HATU) and a base;
wherein, when Y is halogen, the reaction is performed in the presence of triethylamine; and
when Y is halogen in the compound of Chemical Formula 2, the compound of Chemical Formula 2 is prepared by a reaction of the compound of Chemical Formula 2 in which Y is OH with oxalyl halide.

8. A pharmaceutical composition for of treating an ASK-1 mediated disease, comprising the compound according to claim 1 or a pharmaceutically acceptable salt thereof as an active ingredient,
wherein the ASK-1 mediated disease is selected from the group consisting of diabetes, diabetic nephropathy, kidney disease, kidney fibrosis, lung fibrosis, idiopathic pulmonary fibrosis (IPF), liver fibrosis, pulmonary hypertension, chronic obstructive pulmonary disease (COPD), acute lung injury, nonalcoholic steatohepatitis, liver disease, alcoholic liver disease, alcoholic hepatitis, transplantation rejection, a disease accompanying impairment of cartilage turnover, congenital cartilage malformation, a disease associated with hypersecretion of IL6, and a combination thereof.

9. The pharmaceutical composition of claim 8, which inhibits ASK-1 activity.

10. A method for treating an ASK-1 mediated disease, including administering a therapeutically effective amount of the pharmaceutical composition according to claim 8 to a subject in need thereof,
wherein the ASK-1 mediated disease is selected from the group consisting of diabetes, diabetic nephropathy, kidney disease, kidney fibrosis, lung fibrosis, idiopathic pulmonary fibrosis (IPF), liver fibrosis, pulmonary hypertension, chronic obstructive pulmonary disease (COPD), acute lung injury, nonalcoholic steatohepatitis, liver disease, alcoholic liver disease, alcoholic hepatitis, transplantation rejection, a disease accompanying impairment of cartilage turnover, congenital cartilage malformation, a disease associated with hypersecretion of IL6, and a combination thereof.

11. The method of claim 10, wherein the administration of the pharmaceutical composition inhibits ASK-1 activity.

12. The compound of claim 1 or a pharmaceutically acceptable salt thereof, wherein X is NH.

13. The compound of claim 1 or a pharmaceutically acceptable salt thereof, wherein $R_1$ is hydrogen.

14. The compound of claim 1 or a pharmaceutically acceptable salt thereof, wherein $R_2$ or $R_3$ is hydrogen.

15. The compound of claim 1 or a pharmaceutically acceptable salt thereof, wherein X is NH, $R_1$ is hydrogen, and $R_2$ and $R_3$ are each independently hydrogen, $C_{1-6}$ alkyl, $C_{1-6}$ alkoxy, $C_{1-6}$ alkoxy-$C_{1-6}$ alkyl, $C_{6-10}$ aryl, or $C_{5-10}$ heteroaryl.

16. The compound of claim 1 or a pharmaceutically acceptable salt thereof, wherein X is NH, $R_1$ is hydrogen, and $R_2$ and $R_3$ are each independently hydrogen, methyl, ethyl, methoxymethyl, or unsubstituted or substituted phenyl, thiophenyl or pyrimidinyl.

17. The compound of claim 1 or a pharmaceutically acceptable salt thereof, wherein X is NH, $R_1$ is hydrogen, $R_2$ is hydrogen, and $R_3$ is $C_{1-6}$ alkyl, $C_{1-6}$ alkoxy, $C_{1-6}$ alkoxy-$C_{1-6}$ alkyl, $C_{6-10}$ aryl, or $C_{5-10}$ heteroaryl.

18. The compound of claim 1 or a pharmaceutically acceptable salt thereof, wherein X is NH, $R_1$ is hydrogen, $R_3$ is hydrogen, and $R_2$ is $C_{1-6}$ alkyl, $C_{1-6}$ alkoxy, $C_{1-6}$ alkoxy-$C_{1-6}$ alkyl, $C_{6-10}$ aryl, or $C_{5-10}$ heteroaryl.

19. The compound of claim 1 or a pharmaceutically acceptable salt thereof, wherein X is NH, $R_1$ is hydrogen, $R_2$ is hydrogen, and $R_3$ is methyl, ethyl, methoxymethyl, or unsubstituted or substituted phenyl, thiophenyl or pyrimidinyl.

20. The compound of claim 1 or a pharmaceutically acceptable salt thereof, wherein X is NH, $R_1$ is hydrogen, $R_3$ is hydrogen, and $R_2$ is methyl, ethyl, methoxymethyl, or unsubstituted or substituted phenyl, thiophenyl or pyrimidinyl.

\* \* \* \* \*